United States Patent [19]

Kappel et al.

[11] Patent Number: 5,735,890
[45] Date of Patent: Apr. 7, 1998

[54] INFLATABLE BLANKET HAVING ACCESS SLITS

[75] Inventors: Thomas F. Kappel, St. Louis; Philip M. Metzler, St. Charles, both of Mo.

[73] Assignee: Mallinckrodt Medical, Inc., St. Louis, Mo.

[21] Appl. No.: 544,792

[22] Filed: Oct. 18, 1995

[51] Int. Cl.$^6$ ........................................ A61F 7/00
[52] U.S. Cl. .................. 607/104; 607/107; 607/114; 165/46; 126/204; 5/423
[58] Field of Search .................. 607/64, 107, 108, 607/110, 114; 5/421-3, 482, 485; 126/204; 165/46

[56] References Cited

U.S. PATENT DOCUMENTS

| | | |
|---|---|---|
| 630,565 | 8/1899 | Safran . |
| 1,291,191 | 1/1919 | Semple . |
| 1,590,522 | 6/1926 | Kalman . |
| 1,777,982 | 10/1930 | Popp . |
| 2,093,834 | 9/1937 | Gaugler . |
| 2,110,022 | 3/1938 | Kliesrath . |
| 2,122,964 | 7/1938 | Sweetland . |
| 2,235,966 | 3/1941 | Summers . |
| 2,512,559 | 6/1950 | Williams . |
| 2,601,189 | 6/1952 | Wales, Jr. . |
| 2,617,915 | 11/1952 | Blair . |
| 2,700,165 | 1/1955 | Talisman . |
| 2,706,988 | 4/1955 | Weber . |
| 2,791,168 | 5/1957 | Mauch . |
| 2,834,033 | 5/1958 | O'Brien . |
| 2,998,817 | 9/1961 | Armstrong . |
| 3,034,132 | 5/1962 | Landsberger . |
| 3,307,554 | 3/1967 | Thornton et al. . |
| 3,308,850 | 3/1967 | Gill . |
| 3,610,251 | 10/1971 | Sanderson . |
| 3,674,034 | 7/1972 | Hardy . |
| 3,740,777 | 6/1973 | Dee . |
| 3,757,366 | 9/1973 | Sacher . |
| 3,844,339 | 10/1974 | Kranz . |
| 4,026,299 | 5/1977 | Sauder . |
| 4,094,357 | 6/1978 | Sgroi . |
| 4,398,535 | 8/1983 | Guibert . |
| 4,457,295 | 7/1984 | Roehr . |
| 4,572,188 | 2/1986 | Augustine et al. . |
| 4,653,131 | 3/1987 | Diehl . |
| 4,660,388 | 4/1987 | Green, Jr. . |
| 4,777,802 | 10/1988 | Feher . |
| 4,807,644 | 2/1989 | Sandhaus . |
| 4,867,230 | 9/1989 | Voss . |
| 4,959,877 | 10/1990 | Covil . |
| 4,997,230 | 3/1991 | Spitalnick . |
| 5,022,110 | 6/1991 | Stroh . |
| 5,044,364 | 9/1991 | Crowther . |
| 5,097,548 | 3/1992 | Heck et al. . |
| 5,106,373 | 4/1992 | Augustine et al. . |
| 5,125,238 | 6/1992 | Ragan et al. . |

(List continued on next page.)

FOREIGN PATENT DOCUMENTS

| | | |
|---|---|---|
| 1325484 | 12/1993 | Canada . |
| 0311336 | 4/1989 | European Pat. Off. . |
| 149244 | 11/1931 | Switzerland . |
| 85 03216 | 8/1985 | WIPO . |
| 94 03131 | 2/1994 | WIPO . |
| 95 20371 | 8/1995 | WIPO . |
| 95 35077 | 12/1995 | WIPO . |
| 96 03098 | 2/1996 | WIPO . |

*Primary Examiner*—Robert Nasser
*Attorney, Agent, or Firm*—Rothwell, Figg, Ernst & Kurz, P.C.

[57] ABSTRACT

The present invention relates to blankets for use with forced air convection systems, wherein the blankets allow for access to portions of a patient's body before, during or after surgery. In addition, the blankets according to the present invention allow versatility in use by providing access to portions of the patient's body before, during, or after surgery, but which may also completely cover the patient after the surgical procedure is complete. To accomplish these purposes, the blankets according to the present invention include seals or separation lines which extend into the interior of the blanket and which may be separated to allow access to portions of the patient's body.

13 Claims, 3 Drawing Sheets

U.S. PATENT DOCUMENTS

| | | |
|---|---|---|
| 5,165,400 | 11/1992 | Berke . |
| 5,184,612 | 2/1993 | Augustine . |
| 5,265,599 | 11/1993 | Stephenson et al. . |
| 5,300,098 | 4/1994 | Philipot . |
| 5,300,100 | 4/1994 | Hickle et al. . |
| 5,300,101 | 4/1994 | Augustine et al. . |
| 5,300,102 | 4/1994 | Augustine et al. . |
| 5,304,213 | 4/1994 | Berke et al. . |
| 5,304,217 | 4/1994 | Stephenson et al. . |
| 5,318,568 | 6/1994 | Kaufmann et al. . |
| 5,324,320 | 6/1994 | Augustine et al. . |
| 5,336,250 | 8/1994 | Augustine . |
| 5,343,579 | 9/1994 | Dickerhoff et al. . |
| 5,350,417 | 9/1994 | Augustine . |
| 5,360,439 | 11/1994 | Dickerhoff et al. . |
| 5,384,924 | 1/1995 | Dickerhoff et al. . |
| 5,392,847 | 2/1995 | Stephenson . |
| 5,405,370 | 4/1995 | Irani . |
| 5,405,371 | 4/1995 | Augustine et al. . |
| 5,408,712 | 4/1995 | Brun . |
| 5,443,488 | 8/1995 | Namenye et al. . |

INFLATABLE BLANKET HAVING ACCESS SLITS

BACKGROUND

Hypothermia is a condition of subnormal body temperature and presents serious consequences to the patient suffering therefrom. It has been shown that nearly seventy five percent of all patients who undergo surgical procedures develop some degree of hypothermia. This equates to approximately fourteen million patients a year in the United States alone. The hypothermic condition is brought on by many factors including anesthesia, the air conditioning of the operating room, and the infusion of cold blood, I-V solutions, or irrigating fluids.

Several methods and products have been developed to help prevent hypothermia from occurring; such as the use of infrared lamps, cotton blankets, and warm water mattresses. However, none of these methods and products have proven completely successful. In fact, it has been shown that these methods and products can not even prevent the patients from losing their endogenous heat. (See Journal of Post Anesthesia Nursing, Vol. 5, No. 4, August 1990, pp 254–263).

Another method of helping to prevent hypothermia that has proven very effective is the use of forced warm air convection. As early as 1937, a refrigeration blanket using cold air convection was suggested in U.S. Pat. No. 2,093,834 to Gaugler. This blanket included a plurality of layers for channeling airflow from an inlet port. Non-inflatable portions were provided around the periphery of the blanket to secure the blanket around the body.

U.S. Pat. No. 2,512,559 to Williams also relates to a blanket for providing cooled air to a person. The blanket in Williams comprised a plurality of thin sheets of material connected together at a plurality of discrete locations and connected together in a continuous line about the peripheral edge. An air inlet was provided to communicate with space between the sheets to allow cool air to be supplied thereto.

In U.S. Pat. No. 4,572,188 to Augustine, et al., a forced air convection system which can supply either cool or warm air to a blanket is described. The blanket in Augustine, et al. comprises a plurality of inflatable hollow tubes having their interiors connected together through transverse openings. An entry port is provided in the upper surface of the blanket for admitting the cool or warm air and small exit ports are provided through the lower surface to allow the cool or warm air to flow out toward a body covered by the blanket.

Other patents relating to the supply of cool or warm air to a person through an inflatable blanket include U.S. Pat. No. 4,660,388 to Greene, Jr.; U.S. Pat No. 4,777,802 to Feher; and U.S. Pat. No. 4,867,230 to Voss; U.S. Pat. No. 5,125,238 to Ragan et al U.S. Pat. No. 5,300,100 to Hickle et al; U.S. Pat. No. 5,300,102 to Augustine et al; U.S. Pat. No. 5,324,320 to Augustine et al; U.S. Pat. No. 5,343,579 to Dickerhoff et al; U.S. Pat. No. 5,360,439 to Dickerhoff et al; and U.S. Pat. No. 5,384,924 to Dickerhoff et al. Each of these patents describe blankets having various attributes and configurations to supply cool or warm air to the person.

While there are a number of patents noted above and others not mentioned which relate to inflatable blankets for use in supplying cool or warm air to a patient, there remains a need in the art for improvements to forced air convection systems.

OBJECTS OF THE INVENTION

It is one object of the present invention to provide a blanket for a forced air convection system that allows for access to portions of a patient's body, before, during or after surgery.

It is another object of the present invention to provide a blanket for a forced air convection system which provides versatility in use by providing access to portions of the patient's body during surgery, and may also completely cover the patient after the surgical procedure is complete.

SUMMARY OF THE INVENTION

The above objects and others are accomplished according to the present invention by providing a blanket for a forced air convective system which includes a separation line which allows access to portions of the patient's body.

DETAILED DESCRIPTION OF THE INVENTION

Figure 1:
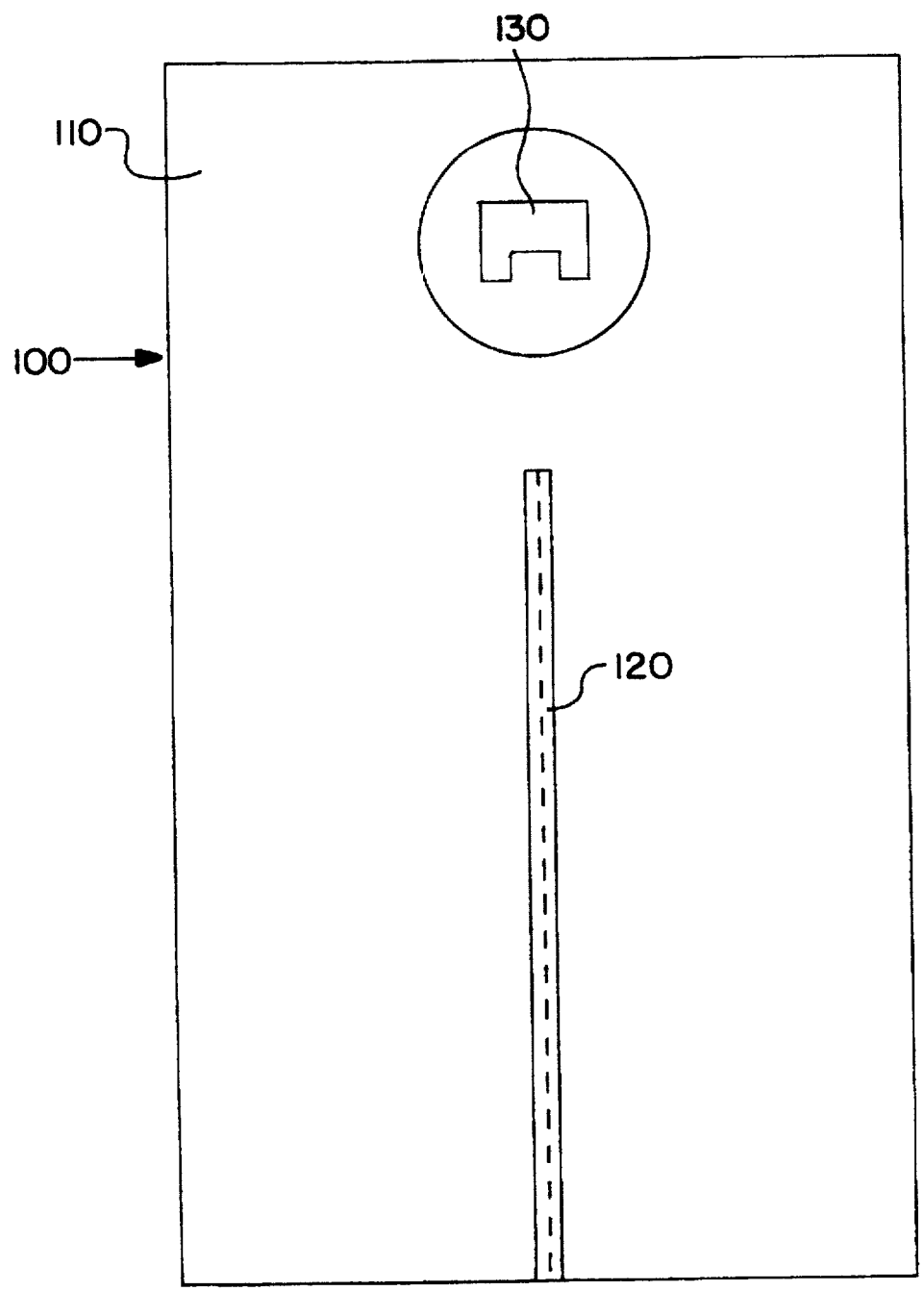
FIG. 1 is a plan view of a blanket for a forced air convection system according to one embodiment of the present invention.

FIG. 1 is a plan view of a blanket, generally designated by reference numeral 100, for a forced air convection system, according to one embodiment of the present invention. In particular, blanket 100, comprises a lower sheet of material (not visible), and an upper sheet of material 110, sealed together around respective peripheral edges to form a cavity therebetween. The lower sheet and upper sheet 110, may further be connected together in any one of several desirable configurations, such as spot welds (see FIG. 2), interconnected columns, interconnected tubes, etc. The blanket 100, includes at least one inlet port 130, for attachment to a source of forced air which will be used to inflate the blanket 100, and provide either warming or cooling air to the patient. As shown in FIG. 1, the inlet port 130, is formed through the surfaces of the blanket 100, at an interior location spaced away from the edges of the blanket 100. Other configurations are equally acceptable and are within the scope of the present invention, as will be further discussed below. The lower sheet of the blanket 100, preferably has a plurality of perforations or small exit holes formed therethrough which allow air to escape from the blanket 100, toward a patient.

The blanket 100, also includes a center line seal 120, extending from a head end of the blanket 100, for a predetermined distance toward a foot end of the blanket 100. The center line seal 120, is formed by sealing the lower sheet to the upper sheet 110, along the center of the blanket 100, for the desired length.

In use the blanket 100, may be separated along center line seal 120, to allow portions of the blanket to be folded away from contact with the patient and thereby reveal desired areas of the patient upon which it may be necessary to perform a surgical or other medical procedure. Separation may be accomplished by cutting through the center line seal 120. Preferably, the center line seal 120, is provided with a perforation which allows the center line 120, to be separated by an easy tearing procedure.

In a preferred embodiment, the blanket 100, includes fastening means, along at least one edge of the center line seal 120, which allow the portions of the blanket 100, separated by the center line seal 120, to be held together when it is desired to cover the patient completely. The fastening means may be of any suitable form, such as tie straps, hook and loop fasteners, buttons, snaps, zippers, adhesives, tape, etc.

The center line seal 120, may extend for any desired length, but preferably extends far enough to enable the entire chest and torso area of the patient to be exposed. Preferably the center line seal 120, extends from about 20 to about 50 inches.

Figure 2:
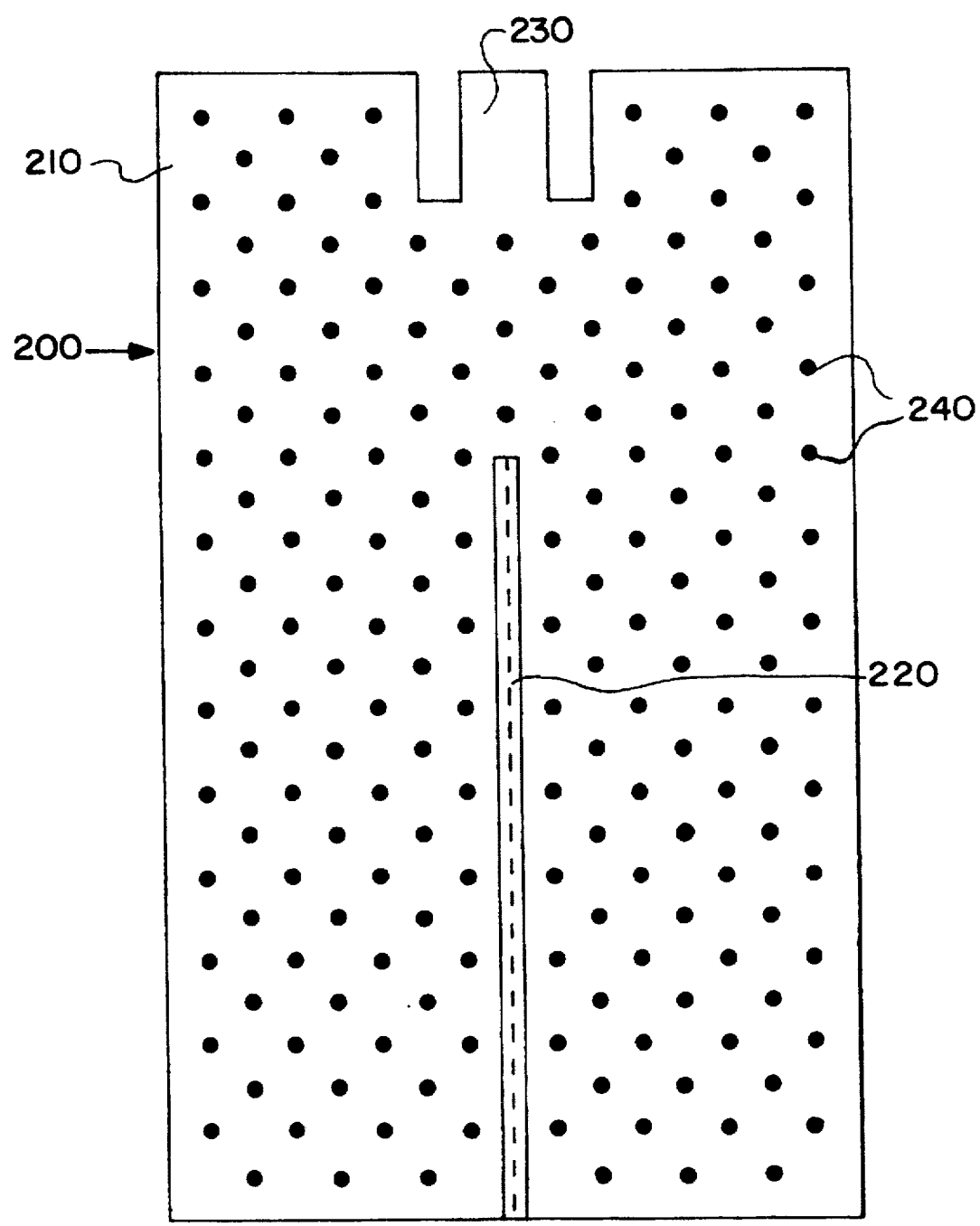
FIG. 2 is a plan view of a blanket for a forced air convection system according to a further embodiment of the present invention.

FIG. 2 is a plan view of a blanket, generally designated by reference numeral 200, for a forced air convection system, according to a further embodiment of the present invention. The blanket 200, comprises a lower sheet of material (not visible), and an upper sheet of material 210, sealed together around respective peripheral edges to form a cavity therebetween. In FIG. 2, the lower sheet and upper sheet 210, are further connected together at a plurality of spot welds 240, which provide a quilt-like pattern to the blanket 200, upon inflation. The blanket 200, includes at least one inlet port 230, which as shown in FIG. 2, is formed along the bottom edge of the blanket 200. The inlet port 230, is attached to a source of forced air which will be used to inflate the blanket 200, and provide either warming or cooling air to the patient. Other locations for the inlet port, 230, are equally acceptable, such as at the corners of the blanket 200, or anywhere along edges of the blanket 200. The lower sheet of the blanket 200, preferably has a plurality of perforations or small exit holes formed therethrough which allow air to escape from the blanket 200, toward a patient.

The blanket 200, also includes a center line seal 220, extending from a head end of the blanket 200, for a predetermined distance toward a foot end of the blanket 200. The center line seal 220, is formed by sealing the lower sheet to the upper sheet 210, along the center of the blanket 200, for the desired length.

In use the blanket 200, may be separated along center line seal 220, to allow portions of the blanket to be folded away from contact with the patient and thereby reveal desired areas of the patient upon which it may be necessary to perform a surgical or other medical procedure. Separation may be accomplished by cutting through the center line seal 220. Preferably, the center line seal 220, is provided with a perforation which allows the center line 220, to be separated by an easy tearing procedure.

In a preferred embodiment, the blanket 200, includes fastening means, along at least one edge of the center line seal 220, which allow the portions of the blanket 200, separated by the center line seal 220, to be held together when it is desired to cover the patient completely. The fastening means may be of any suitable form, such as tie straps, hook and loop fasteners, buttons, snaps, zippers, adhesives, tape, etc.

The center line seal 220, may extend for any desired length, but preferably extends far enough to enable the entire chest and torso area of the patient to be exposed. Preferably the center line seal 220, extends from about 20 to about 50 inches.

Figure 3:
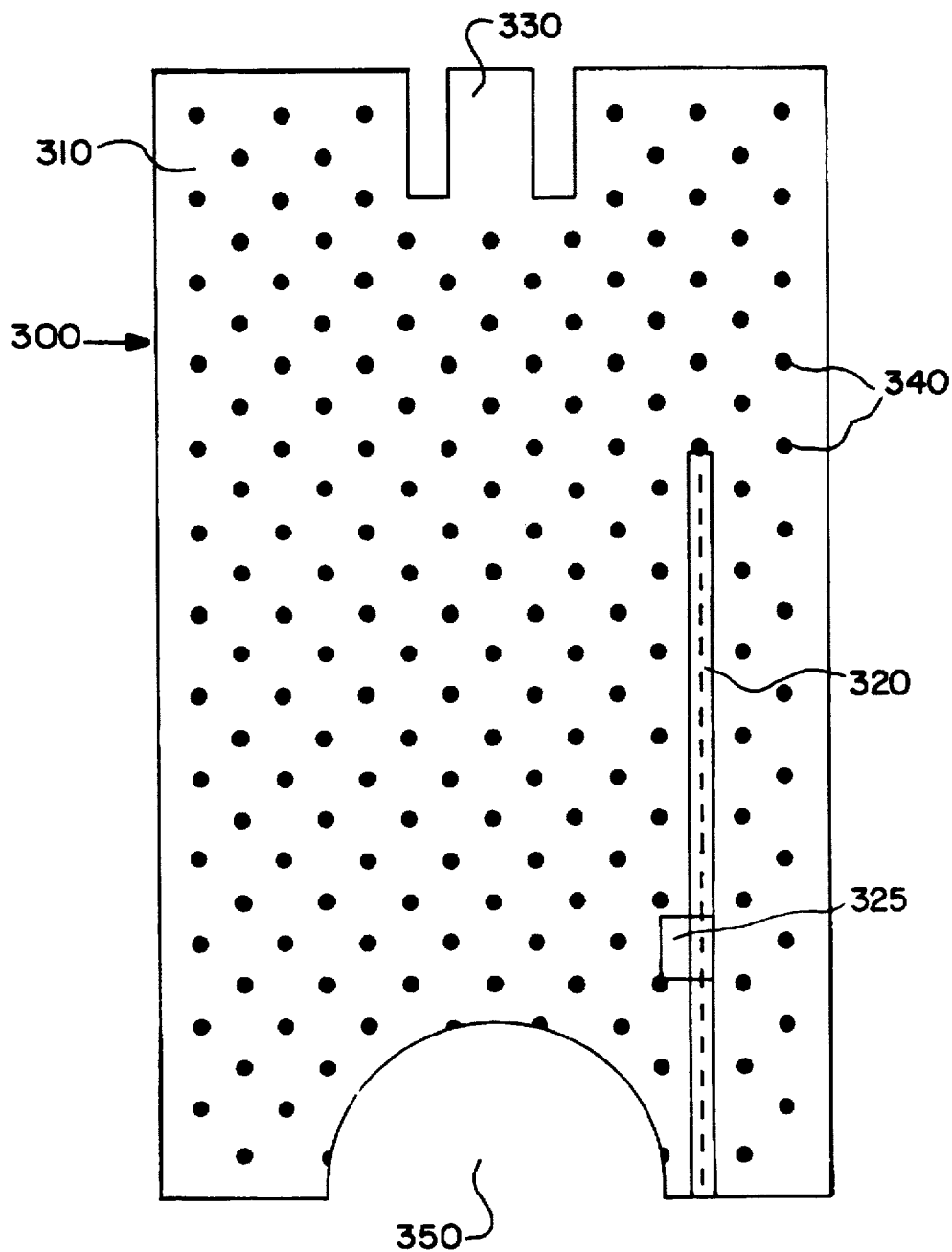
FIG. 3 is a plan view of a blanket for a forced air convection system according to another embodiment of the present invention.
Figure 4:
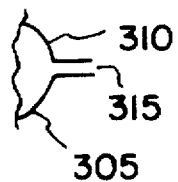
FIG. 4 is a schematic side elevation view, with portions broken away, of a blanket in accordance with one embodiment of the present invention.

FIG. 3 is a plan view of a blanket, generally designated by reference numeral 300, for a forced air convection system, according to a further embodiment of the present invention. The blanket 300, comprises a lower sheet of material 305, and an upper sheet of material 310, sealed together around respective peripheral edges 315 to form a cavity therebetween, see also FIG. 4. In FIG. 3, the lower sheet and upper sheet 310, are further connected together at a plurality of spot welds 340, which provide a quilt-like pattern to the blanket 300, upon inflation. The blanket 300, includes at least one inlet port 330, which as shown in FIG. 3, is formed along the bottom edge of the blanket 300. The inlet port 330, is attached to a source of forced air which will be used to inflate the blanket 300, and provide either warming or cooling air to the patient. Other locations for the inlet port 330, are equally acceptable, such as at the corners of the blanket 300, or anywhere along edges of the blanket 300. The lower sheet of the blanket 300, preferably has a plurality of perforations or small exit holes formed therethrough which allow air to escape from the blanket 300, toward a patient.

The blanket 300, also includes a separation seal 320, extending from a head end of the blanket 300, for a predetermined distance toward a foot end of the blanket 300. The separation seal 320, is offset from the center of the blanket 300, and is formed by sealing the lower sheet to the upper sheet 310, for the desired length.

In use the blanket 300, may be separated along separation seal 320, to allow portions of the blanket to be folded away from contact with the patient and thereby reveal desired areas of the patient upon which it may be necessary to perform a surgical or other medical procedure. Separation may be accomplished by cutting through the separation seal 320. Preferably, the separation seal 320, is provided with a perforation which allows the separation seal 320, to be separated by an easy tearing procedure.

In a preferred embodiment, the blanket 300, includes fastening means, along at least one edge of the separation seal 320, which allow the portions of the blanket 300, separated by the separation seal 320, to be held together when it is desired to cover the patient completely. The fastening means may be of any suitable form, such as tie straps, hook and loop fasteners, buttons, snaps, zippers, adhesives, tape, etc, as represented schematically by fastening means 325 shown in FIG. 3.

The separation seal 320, may extend for any desired length, but preferably extends from about 20 to about 50 inches.

Also in a preferred embodiment, the blanket 300, includes a head cut out area 350, for accommodating the patients head when blanket 300, is in use.

The provision of the center line seal in the blankets according to the present invention enable use of the blankets in a wide variety of configurations. In particular, the center line seal may be only partially opened so that a limited portion of the patient is exposed, or the center line seal may be fully opened if a greater portion of the patient is to be exposed. Even if the center line seal is fully opened, it is still possible to expose smaller portions of the patient, simply by folding less of the blanket back.

The invention has been described above with reference to a center line seal. However, the present invention is equally applicable to any seal which would aid in exposing selective portions of a patient. As shown in FIGS. 1 and 2, the center line seal extends from the head end of the blanket. However, a seal could extend from any edge of the blanket, including the foot end, or either side of the blanket. Additionally, multiple seals could be provided in any of the configurations noted above. Also, these seals may extend along parallel lines with respect to the edges of the blanket or may extend at different angles into the interior of the blanket.

Seals may also be provided entirely within the interior of the blanket, rather then extending from an edge. Such seals may be opened to allow tubes or other medical apparatus to be admitted or egressed therethrough. Preferably, such seals would be in the form of a cross or "X" so that the opening could be sufficiently opened to serve its purpose. Such a seal would also allow very specific portions of the patient to be revealed.

As noted above, the inlet port may be formed at almost any position which allows inflation medium to be introduced to the interior of the blanket. In particular, the inlet port may be provided along an edge of the blanket, at a corner of the blanket, or through the upper or lower sheet of the blanket within the interior surface area thereof.

The blankets according to the present invention provide for great versatility of use. In particular, the blankets of the present invention allow for access to portions of a patient's body during surgery. Further, the blankets of the present invention provide access to portions of the patient's body during surgery, but may also completely cover the patient after the surgical procedure is complete.

The blankets shown in FIGS. 1 and 2 represent full body blankets but the present invention would be equally applicable to blankets intended to cover only portions of the patient, such as an upper body blanket or a lower body blanket. The blankets according to the present invention are also equally useful in both adult and pediatric sizes. The blankets above have been described primarily as relating to blankets for use in the operating room, however, it will be recognized that the present invention is equally applicable for blankets to be used in other areas of the hospital, such as the PACU. Moreover, as noted, the blankets according to the present invention may be used to provide either warming or cooling to a patient.

The blankets of the present invention may be formed of any suitable material capable of being sealed together at selected positions and having sufficient strength to allow inflation and adequate air distribution within the inflated portion. Such materials include plastics, plastic non-wovens, wood pulp compositions, laminated plastic and wood pulp materials, and combinations thereof.

The foregoing has been a description of certain preferred embodiments of the present invention, but is not intended to limit the invention in any way. Rather, malay modifications, variations and changes in details may be made within the scope of the present invention.

What is claimed is:

1. An inflatable blanket for a forced air convection system comprising:

an upper sheet of material having a generally rectangular shape with an upper end, a lower end and two sides;

a lower sheet of material having a generally rectangular shape with an upper end, a lower end and two sides;

wherein said upper sheet and said lower sheet are sealed together around their peripheral edges at their respective upper ends, lower ends and sides, to create an inflatable cavity having an upper end, a lower end, and two sides therebetween;

an inflation port connecting said inflatable cavity with the atmosphere and through which inflation medium may be introduced to said inflatable cavity to inflate said blanket; and wherein said upper sheet and said lower sheet are further sealed together along at least one separable seal line, such that when said separable seal line is separated, portions of said blanket may be moved independently of other portions of said blanket so as to expose desired areas of a patient on which said blanket is being utilized, further including fastening means located along at least one edge of said seal line for holding portions of said blanket on opposite sides of said seal line together after said seal line has been separated.

2. A blanket according to claim 1, wherein said seal line extends from said upper end toward said lower end of said inflatable cavity and is located approximately midway between said sides of said inflatable cavity.

3. A blanket according to claim 2, wherein said seal line extends for a distance of about 20 to about 50 inches.

4. A blanket according to claim 3, wherein said seal line extends for about 20 inches.

5. A blanket according to claim 3, wherein said seal line extends for about 50 inches.

6. A blanket according to claim 1, wherein said seal line extends from one of said upper end, said lower end, or said sides of said inflatable cavity, and extends in a parallel line to said upper end, said lower end, or said sides of said inflatable cavity.

7. A blanket according to claim 1, wherein said blanket includes multiple seal lines.

8. A blanket according to claim 1, wherein said seal line includes a perforation along which said seal line is separable.

9. A blanket according to claim 1, wherein said fastening means are selected from the group consisting of tie straps, hook and loop fasteners, buttons, snaps, zippers, adhesives, and tape.

10. A blanket according to claim 1, wherein said upper sheet and said lower sheet are further connected together by means selected from the group consisting of spot welds.

11. A blanket according to claim 1, wherein said inflation port is provided through said upper sheet at a location within the interior surface area of said blanket.

12. A blanket according to claim 1, wherein said inflation port is provided along, said lower end.

13. A blanket according to claim 1, wherein said blanket includes a head cut out area.

* * * * *